US011510577B2

(12) United States Patent
Bozsak et al.

(10) Patent No.: US 11,510,577 B2
(45) Date of Patent: Nov. 29, 2022

(54) MEDICAL DEVICE PROVIDED WITH SENSORS

(71) Applicant: Sensome SAS, Massy (FR)

(72) Inventors: Franz Bozsak, Versailles (FR); Bruno Carreel, Paris (FR); Pierluca Messina, Paris (FR); Myline Cottance, Paris (FR)

(73) Assignee: Sensome SAS, Massy (FR)

( * ) Notice: Subject to any disclaimer, the term of this patent is extended or adjusted under 35 U.S.C. 154(b) by 1086 days.

(21) Appl. No.: 16/091,766

(22) PCT Filed: Apr. 5, 2017

(86) PCT No.: PCT/EP2017/058169
§ 371 (c)(1),
(2) Date: Oct. 5, 2018

(87) PCT Pub. No.: WO2017/174688
PCT Pub. Date: Oct. 12, 2017

(65) Prior Publication Data
US 2019/0159684 A1 May 30, 2019

(30) Foreign Application Priority Data
Apr. 6, 2016 (FR) ...................................... 1653032

(51) Int. Cl.
*A61B 5/02* (2006.01)
*A61B 5/00* (2006.01)
(Continued)

(52) U.S. Cl.
CPC ........ *A61B 5/02007* (2013.01); *A61B 5/0031* (2013.01); *A61B 5/02158* (2013.01);
(Continued)

(58) Field of Classification Search
CPC ... A61B 5/0031; A61B 5/6862; A61B 5/0538; H04L 67/12
See application file for complete search history.

(56) References Cited

U.S. PATENT DOCUMENTS 5,800,350 A    9/1998   Coppleson et al.
5,938,624 A    8/1999   Akerfeldt et al.
(Continued)

FOREIGN PATENT DOCUMENTS

CA    2814557 A1    4/2012
CN    1329290 A     1/2002
(Continued)

OTHER PUBLICATIONS

EP 15771665.5, Feb. 2, 2020, European Communication.
(Continued)

*Primary Examiner* — Douglas X Rodriguez
*Assistant Examiner* — Sangkyung Lee
(74) *Attorney, Agent, or Firm* — Greenberg Traurig, LLP; Andrew J. Tibbetts

(57) ABSTRACT

The invention relates to a medical device (12) comprising an electrical measurement circuit (16), in which are connected at least two variable-impedance sensors (22), the impedance of which varies according to a detected physical quantity, an electrical power source (18) for supplying power to the electrical measurement circuit (16), an antenna (18) for emitting an electromagnetic field according to the impedance of the electrical measurement circuit (16), each of the sensors (22) being associated with a switch (24) for interrupting the current supply of the sensor (22) in said measurement circuit (16), the medical device (12) additionally comprising a system (26) for controlling the switches (24) in order to successively control the opening or the closing of the switches (24), according to determined configurations.

(Continued)

The medical device (12) may in particular be applied to the human body or implanted within the human body.

26 Claims, 9 Drawing Sheets

(51) Int. Cl.
    *A61B 5/0215*     (2006.01)
    *A61F 2/90*     (2013.01)
    *H04L 67/12*     (2022.01)
    *A61B 5/06*     (2006.01)
    *H01F 38/32*     (2006.01)
    *A61B 5/0538*     (2021.01)

(52) U.S. Cl.
    CPC ............ *A61B 5/065* (2013.01); *A61B 5/4851* (2013.01); *A61B 5/6862* (2013.01); *A61B 5/6876* (2013.01); *A61F 2/90* (2013.01); *H04L 67/12* (2013.01); *A61B 5/0538* (2013.01); *A61B 2560/02* (2013.01); *A61B 2560/0238* (2013.01); *A61B 2562/046* (2013.01); *A61B 2562/085* (2013.01); *A61F 2240/00* (2013.01); *A61F 2250/0002* (2013.01); *H01F 38/32* (2013.01)

(56) References Cited

U.S. PATENT DOCUMENTS

| | | | |
|---|---|---|---|
| 6,063,028 A | 5/2000 | Luciano | |
| 6,090,052 A | 7/2000 | Akerfeldt et al. | |
| 6,106,486 A | 8/2000 | Tenerz et al. | |
| 6,112,598 A | 9/2000 | Tenerz et al. | |
| 6,206,835 B1 | 3/2001 | Spillman, Jr. et al. | |
| 6,428,336 B1 | 8/2002 | Akerfeldt | |
| 6,437,551 B1 | 8/2002 | Krulevitch et al. | |
| 6,461,301 B2 | 10/2002 | Smith | |
| 6,679,269 B2 | 1/2004 | Swanson | |
| 7,792,588 B2 * | 9/2010 | Harding | A61N 1/37288 607/60 |
| 7,991,484 B1 * | 8/2011 | Sengupta | A61N 1/3702 607/126 |
| 8,233,979 B1 | 7/2012 | Shelchuk | |
| 8,277,386 B2 | 10/2012 | Ahmed et al. | |
| 8,478,378 B2 | 7/2013 | Lal et al. | |
| 8,491,567 B2 | 7/2013 | Magnin et al. | |
| 8,777,898 B2 | 7/2014 | Suon et al. | |
| 8,840,560 B2 | 9/2014 | Hossack et al. | |
| 9,048,752 B2 * | 6/2015 | Capilla | H02M 1/4225 |
| 9,121,806 B1 | 9/2015 | Bhansali et al. | |
| 9,301,699 B2 | 4/2016 | Hubinette et al. | |
| 2002/0043113 A1 | 4/2002 | Tulkki et al. | |
| 2002/0077627 A1 | 6/2002 | Johnson et al. | |
| 2002/0177782 A1 | 11/2002 | Penner | |
| 2003/0030499 A1 * | 2/2003 | Huang | H03K 3/0231 331/111 |
| 2004/0127960 A1 | 7/2004 | Mass et al. | |
| 2005/0065592 A1 | 3/2005 | Holzer | |
| 2006/0047205 A1 | 3/2006 | Ludomirsky et al. | |
| 2006/0254600 A1 | 11/2006 | Danek et al. | |
| 2007/0255145 A1 | 11/2007 | Smith et al. | |
| 2007/0255270 A1 | 11/2007 | Carney | |
| 2008/0180345 A1 * | 7/2008 | Larson | H01Q 1/273 343/861 |
| 2008/0262489 A1 | 10/2008 | Steinke | |
| 2009/0118808 A1 | 5/2009 | Belacazar et al. | |
| 2009/0267588 A1 * | 10/2009 | Schmitz | H02J 1/14 323/352 |
| 2010/0191141 A1 | 7/2010 | Aberg | |
| 2011/0054583 A1 | 3/2011 | Litt et al. | |
| 2011/0251469 A1 | 10/2011 | Varadan | |
| 2012/0016206 A1 | 1/2012 | Ramarajan et al. | |
| 2012/0036689 A1 | 2/2012 | Sjosten et al. | |
| 2012/0061257 A1 | 3/2012 | Yu et al. | |
| 2012/0172731 A1 | 7/2012 | Smith | |
| 2012/0190989 A1 | 7/2012 | Kaiser et al. | |
| 2012/0283714 A1 * | 11/2012 | Mihalik | A61B 18/02 606/21 |
| 2012/0316454 A1 | 12/2012 | Carter | |
| 2013/0274712 A1 | 10/2013 | Schecter | |
| 2013/0282084 A1 | 10/2013 | Mathur et al. | |
| 2014/0005558 A1 | 1/2014 | Gregorich | |
| 2014/0058197 A1 | 2/2014 | Salahieh et al. | |
| 2014/0058275 A1 | 2/2014 | Gregorich et al. | |
| 2014/0066790 A1 | 3/2014 | Burkett et al. | |
| 2014/0066791 A1 | 3/2014 | Burkett | |
| 2014/0081244 A1 | 3/2014 | Voeller et al. | |
| 2014/0180031 A1 | 6/2014 | Anderson | |
| 2014/0276109 A1 | 9/2014 | Gregorich | |
| 2014/0276223 A1 | 9/2014 | Gustafsson | |
| 2014/0284422 A1 | 9/2014 | Sapir | |
| 2014/0343382 A1 | 11/2014 | Kersey et al. | |
| 2014/0343629 A1 * | 11/2014 | Kaula | G06F 3/0485 607/59 |
| 2015/0032011 A1 | 1/2015 | McGowan et al. | |
| 2015/0051499 A1 | 2/2015 | McGowan | |
| 2015/0123679 A1 * | 5/2015 | Kuyvenhoven | H04B 5/0081 324/652 |
| 2015/0209526 A1 | 7/2015 | Matsubara et al. | |
| 2015/0297807 A1 | 10/2015 | Leblanc et al. | |
| 2015/0305649 A1 * | 10/2015 | Cohen | A61B 5/053 600/407 |
| 2015/0313478 A1 | 11/2015 | Veszelei et al. | |
| 2016/0051323 A1 | 2/2016 | Stigall et al. | |
| 2016/0058382 A1 | 3/2016 | Burkett et al. | |
| 2016/0058977 A1 | 3/2016 | Burkett et al. | |
| 2016/0073957 A1 | 3/2016 | Szunyog | |
| 2016/0077030 A1 * | 3/2016 | Stanley | G01N 27/122 324/650 |
| 2016/0121085 A1 | 5/2016 | Burkett et al. | |
| 2016/0287178 A1 | 10/2016 | Ranganathan et al. | |
| 2016/0303354 A1 | 10/2016 | Burkett et al. | |
| 2018/0235545 A1 | 8/2018 | Barakat et al. | |

FOREIGN PATENT DOCUMENTS

| | | |
|---|---|---|
| CN | 1576862 A | 2/2005 |
| CN | 1788677 A | 6/2006 |
| CN | 101004424 A | 7/2007 |
| CN | 102370476 A | 3/2012 |
| CN | 102481110 A | 5/2012 |
| DE | 101 03 503 A1 | 8/2002 |
| DE | 10103503 A | 8/2002 |
| EP | 2271933 B1 | 12/2012 |
| JP | 2000-271101 A | 10/2000 |
| JP | 2003-532440 A | 11/2003 |
| JP | 2004-41724 A | 2/2004 |
| JP | 2008-526293 A | 7/2008 |
| JP | 2011-513038 A | 4/2011 |
| JP | 2013-502278 A | 1/2013 |
| JP | 2013-510374 A | 3/2013 |
| JP | 2013-539692 A | 10/2013 |
| WO | WO 99/42176 A1 | 8/1999 |
| WO | WO 00/56210 A1 | 9/2000 |
| WO | WO 01/37726 A1 | 5/2001 |
| WO | WO 03/057011 A2 | 7/2003 |
| WO | WO 2006/070369 A2 | 7/2006 |
| WO | WO 2006/113747 A2 | 10/2006 |
| WO | WO 2009/103156 A1 | 8/2009 |
| WO | WO 2009/114689 A1 | 9/2009 |
| WO | WO 2009/136157 A2 | 11/2009 |
| WO | WO 2009/136167 A1 | 11/2009 |
| WO | WO 2011/022418 A2 | 2/2011 |
| WO | WO 2011/057024 A2 | 5/2011 |
| WO | WO 2011/121581 A1 | 10/2011 |
| WO | WO 2016/050972 A1 | 4/2016 |

OTHER PUBLICATIONS

U.S. Appl. No. 15/516,531, filed Apr. 3, 2017, Barakat et al.
FR 1459531, Oct. 3, 2014, Written Opinion on Patentability.

(56) References Cited

OTHER PUBLICATIONS

FR 1459531, Jun. 30, 2015, Preliminary Search Report.
FR 1560174, Oct. 23, 2015, Written Opinion on Patentability.
FR 1560174, Jun. 17, 2016, Preliminary Search Report.
PCT/EP2015/072859, Dec. 3, 2015, International Search Report and Written Opinion.
PCT/EP2015/072859, Apr. 13, 2017, International Preliminary Report on Patentability.
PCT/EP2016/075456, Dec. 9, 2016, International Search Report and Written Opinion.
PCT/EP2016/075456, May 3, 2018, International Preliminary Report on Patentability.
PCT/EP2017/058169, Jun. 2, 2017, International Search Report and Written Opinion.
PCT/EP2017/079960, Apr. 5, 2018, International Search Report and Written Opinion.
PCT/IB2017/001230, May 4, 2018, International Search Report and Written Opinion.
French Communication for French Application No. 1459531 dated Oct. 3, 2014.
French Communication for French Application No. 1459531 dated Jun. 30, 2015.
Written Opinion on Patentability for French Application No. 1560174 dated Oct. 23, 2015.
Preliminary Search Report for French Application No. 1560174 dated Jun. 17, 2016.
International Search Report and Written Opinion for International Application No. PCT/EP2015/072859 dated Dec. 3, 2015.
International Preliminary Report on Patentability for International Application No. PCT/EP2015/072859 dated Apr. 13, 2017.
International Search Report and Written Opinion for International Application No. PCT/EP2016/075456 dated Dec. 9, 2016.
International Preliminary Report on Patentability for International Application No. PCT/EP2016/075456 dated May 3, 2018.
International Search Report and Written Opinion for International Application No. PCT/EP2017/058169 dated Jun. 21, 2017.
International Search Report and Written Opinion for International Application No. PCT/EP2017/079960 dated Apr. 5, 2018.
International Search Report and Written Opinion for International Application No. PCT/IB2017/001230 dated May 4, 2018.
[No Author Listed], Electronique et informatique. Daniel Robert. http://www.electronique-et-informatique.fr/anglais/Digit/Digit_8T.html Sep. 22, 2006. Last accessed Aug. 7, 2018. 9 pages.
[No Author Listed], Ring oscillator. https://en.wikipedia.org/w/index.php?title=Ring_oscillator&oldid=674008095 Aug. 1, 2015. Last accessed Aug. 7, 2018. 4 pages.
Bilge et al., Label-Free Recognition of Drug Resistance via Impedimetric Screening of Breast Cancer Cells. Plos One. 2013;8(3).
Nguyen et al., A cell impedance sensor chip for cancer cells detection with single cell resolution. 2013 IEEE Sensors. Nov. 3, 2013. 1-4.
Srinivasaraghavan et al., Microelectrode bioimpedance analysis distinguishes basal and claudin-low subtypes of triple negative breast cancer cells. Biomedical Microdevices. 2015;17(4):1-11.
Xu et al., A review of impedance measurements of whole cells. Biosensors and Bioelectronics. Oct. 22, 2015. vol. 77. 824-836.
European Communication for European Application No. 15771665.5 dated Feb. 5, 2020.
Arndt et al., Bioelectrical impedance assay to monitor changes in cell shape during apoptosis. Biosensors and Bioelectronics. 2004;19:583-94.

Brug et al., The Analysis of Electrode Impedances Complicated by the Presence of a Constant Phase Element. Journal of Electroanalytical Chemistry and Interfacial Electrochemistry. 1984;176:275-95.
Chauveau et al., Ex Vivo Discrimination between Normal and Pathological Tissues in Human Breast Surgical Biopsies Using Bioimpedance Spectroscopy. Annals of the New York Academy of Sciences. 1999;873:42-50.
Cho et al., Chip-based time-continuous monitoring of toxic effects on stem cell differentiation. Annals of Anatomy. 2009;191:145-52.
Cho et al., Electrical characterization of human mesenchymal stem cell growth on microelectrode. Microelectronic Engineering. Science Direct. 2008;85:1272-4.
Cho et al., Impedance monitoring of herpes simplex virus-induced cytopathic effect in Vero cells. Elsevier. Sensors and Actuators B. 2007;123:978-82.
Cole et al., Dispersion and Absorption in Dielectrics. Journal of Chemical Physics. 1941;9:341-51.
Franks et al., Impedance Characterization and Modeling of Electrodes for Biomedical Applications. Biomedical Engineering. IEEE Transactions on Biomedical Engineering. 2005;52(7):1295-1302.
Giaever et al., A morphological biosensor for mammalian cells. Nature. 1993;366:591-2.
Giaever et al., Micromotion of mammalian cells measured electrically. Proceedings of the National Academy of Sciences. 1991;88:7896-900.
Grimnes et al., Bioimpedance and Bioelectricity Basics. Academic. Elsevier. Second Edition. 2000. 484 pages.
Helen et al., Investigation of tissue bioimpedance using a macro-needle with a potential application in determination of needle-to-nerve proximity. Proceedings of the 8th International Conference on Sensing Technology. Sep. 2-4, 2014. 376-80.
Hilderbrandt et al., Detection of the osteogenic differentiation of mesenchymal stem cells in 2D and 3D cultures by electrochemical impedance spectroscopy. Journal of Biotechnology. 2010;148:83-90.
Hirschorn et al., Determination of effective capacitance and film thickness from constant-phase-element parameters. Electrochimica Acta. 2010;55:6218-27.
Linderholm et al., Two-dimensional impedance imaging of cell migration and epithelial stratification. Lab on a Chip. Paper. 2006;6:1155-62.
Luong et al., Monitoring Motility, Spreading, and Mortality of Adherent Insect Cells Using an Impedance Sensor. Analytical Chemistry. 2001;73:1844-8.
Orazem et al., Dielectric Properties of Materials Showing Constant-Phase-Element (CPE) Impedance Response. Journal of the Electrochemcial Society. 2013;160(6):C215-C225.
Orazem et al., Electrochemical Impedance Spectroscopy. John Wiley & Sons, Inc. 2008. 533 pages.
Pauly et al., Electrical Properties of Mitochondrial Membranes. The Journal of Biophysical and Biochemical Cytology. 1960;7(4):589-601.
Qiao et al., Bioimpedance Analysis for the Characterization of Breast Cancer Cells in Suspension. Biomedical Engineering. IEEE Transactions. 2012;59:2321-90.
Rigaud et al., In vitro tissue characterization and modelling using electrical impedance measurements in the 100 Hz-10 MHz frequency range. Physiological Measurement. 1995;16:A15-A28.
Schade-Kampmann et al., On-chip non-invasive and label-free cell discrimination by impedance spectroscopy. Cell Prolif, 2008;41:830.40.
Xiao et al., Assessment of Cytotoxicity Using Electric Cell-Substrate Impedance Sensing: Concentration and Time Response Function Approach. Analytical Chemistry. 2002;74:5748-53.

* cited by examiner

FEUILLE DE REMPLACEMENT (RÈGLE 26)

MEDICAL DEVICE PROVIDED WITH SENSORS

RELATED APPLICATIONS

This Application is a national stage filing under 35 U.S.C. 371 of International Patent Application Serial No. PCT/EP2017/058169, filed Apr. 5, 2017, titled "MEDICAL DEVICE PROVIDED WITH SENSORS", which claims priority to French application number 1653032, filed Apr. 6, 2016, the entire contents of each of which is incorporated herein by reference.

The present invention relates to a medical device provided with sensors. The invention also relates to a medical system comprising such a medical device and a method for querying such a medical device, particularly in a medical system.

The invention particularly relates to an implantable medical device such as a stent (sometimes also referred to as "arterial endoprosthesis", "vascular stent", or simply "spring") provided with sensors.

A stent is a device of tubular shape produced by a deformable mesh, particularly made of metal or of a biodegradable polymer material. The stent is inserted into a patient's body in a folded state, with the meshes closed, and is then extended inside the patient's body, for example by angioplasty which triggers the deployment of the meshes. The stent, once deployed, helps keep a cavity open in the patient's body. It is known that fitting a stent may particularly cause tissue inflammation, hyperplasia and/or blood clotting.

Consequently, a stent may be provided with sensors, which make it possible to monitor the state of the tissues around the stent to, optionally, adapt the patient's treatment accordingly. Sensors may also be provided to ensure that the stent fulfils the function thereof of keeping a cavity open.

It is known to query a stent, i.e. collect information from this stent, using a contactless querying device, retained outside the patient. Generally, such a contactless querying device is configured to measure an electromagnetic field emitted by the stent implanted in the patient.

The patent EP-B-2 271 933 as such describes a method for characterising cells in the vicinity of a medical device implanted in a patient, particularly a stent, using impedance measurements at different frequencies.

The application WO-A-2009/1 361 677 describes an implantable medical device such as a stent, having an electrically conductive surface and an impedance sensor for measuring the impedance of the conductive surface of the implantable medical device, at different frequencies, using the conductive surface as an electrode. The measurements made are used to determine the degree of restenosis of the tissues at the level of the implantable device, i.e. the tissue thickness having grown at the level of the conductive surface of the implantable medical device.

These documents disclose methods providing overall information on the implantable device, without making it possible to obtain independently the measurements made by each sensor with which the implantable medical device is provided.

Moreover, it is known from U.S. Pat. No. 8,478,378, a stent provided with sensors distributed on the inner surface thereof, oriented towards the passage through the stent, or "luminal" surface. The sensors are configured to send a specific characteristic output signal in response to an excitation. The specific characteristic signal may particularly be a wavelength specific to each of the sensors. U.S. Pat. No. 8,478,378 indicates that as such an output signal including signals from all or most of the sensors suggests that a large number of sensors are not coated with a layer of endothelial cells.

The application DE-A-101 03 503 discloses a stent comprising electrodes for measuring the impedance of tissue in contact with the stent where each set of electrodes is associated with a multiplexer controlled by a control circuit. Implanting such multiplexers renders the stent structure complex.

It is known from the applications US-A-2011/0054583 and US-A-2012/0190989 a sensor array topology in a stent. Such a topology enables addressing of the sensors by row and by column, enabling activation of the sensors in a reconfigurable manner and independently from one another.

Finally, the application WO-A-2011/121581 describes an implantable medical device capable of responding to an electromagnetic query field emitted by a remote querying device. The implantable medical device is provided with a plurality of modulators consisting of RFID ("Radio-Frequency Identification") chips, RFID chips are suitable for the implantable medical device to respond to an electromagnetic query field according to a modulation generating a unique respective identification code.

The use of RFID chips as sensors in the medical device limits however the number of sensors with which it may be provided. The multiplication of the RFID chips indeed increases the price of the medical device accordingly. Moreover, according to this document, the medical device must be at least partially made of a metallic material having good electrical conduction. Finally, according to this document, the RFID chips must be implanted in the very structure of the implantable medical device, rendering the embodiment thereof particularly complex.

Implantable medical devices are also known from WO-A-01/37 726 or U.S. Pat. No. 6,206,835. These medical devices include a structure implantable in the body to assist with carrying out a vital function in the body. One or a plurality of sensors are associated with this implantable structure, which make(s) it possible to measure a parameter associated with the structure. Finally, these medical devices include a communication circuit coupled with the sensor(s) to deliver a signal according to the parameter measured and to transmit this signal to a receiving device, outside the body, non-invasively.

The aim of the invention is that of remedying the problems mentioned above. In particular, the aim of the invention is that of providing a medical device having a simple structure and therefore limited cost, suitable for distinguishing the quantities measured by various sensors with which the medical device is provided. In one preferred embodiment, the medical device is implantable in the patient's body and configured to make it possible to determine, without intruding the patient's body, whether it is implanted correctly.

The invention relates to a medical device comprising an electrical measurement circuit, wherein are connected at least two variable-impedance sensors according to a detected physical quantity, an electrical power source for supplying power to the electrical measurement circuit, an antenna for emitting an electromagnetic field according to the impedance of the electrical measurement circuit, each of the sensors being associated with a switch for interrupting the current supply of the sensor in said measurement circuit, the medical device further comprising a system for controlling the switches in order to successively control the opening or the closing of the switches, according to determined configurations.

As such, according to the invention, the medical device is provided with any type of variable-impedance sensors connected to one another in a so-called measurement circuit. A control system makes it possible to switch off the current supply of the various sensors according to predetermined configurations, such that the electromagnetic field emitted by the medical device corresponds to the configuration of the measurement circuit. By carrying out successive measurements, corresponding to linearly independent configurations—for example one sensor disconnected from the circuit at a time or all the sensors disconnected from the circuit at a time except one—it is very readily possible to obtain qualitative information on the values measured by each of the sensors of the medical device, arranged at known locations on the medical device.

The term "disconnecting a sensor from the circuit" denotes hereinafter creating a circuit configuration such that the current passing through the sensor is nil, the other sensors being capable of being supplied with current. The sensor is for example disconnected from the circuit by being short-circuited per se or disconnected from the circuit by opening the sensor circuit, i.e. the sensor is disconnected from the circuit thereof. In other words, "disconnecting a sensor from the circuit", in both scenarios, denotes herein switching off the current supply of this sensor.

Preferably, the medical device includes one or a plurality of the following features taken alone or in combination:
- the medical device is implantable in the human body or can be applied on the human body;
- each switch is formed by one or more transistors, particularly one or more field-effect transistors FET, more particularly one or more metal-oxide-semiconductor field-effect transistors MOS-FET, enhancement or depletion mode, N-channel or P-channel type, one or more MEMS, or one or more mechanical switches;
- the system for controlling the switches includes a control circuit, powered by the electrical power source, and configured, preferably, to control successively the opening or closing of the various switches, one after the other;
- the control system includes components implanted directly in the measurement circuit, preferably to control successively the opening or closing of the various switches, one after the other;
- the control system includes modules having the same structure, arranged in series with respect to one another, each controlling an associated switch;
- the input of the first module controls successively the opening or closing of the various switches, one after the other; in other words, a change of status of this input triggers, after some time, a change of status at the output of the module corresponding to the input of the next module;
- each module includes a series RC circuit the charging or discharging whereof triggers the closing or opening of the associated switch;
- charging or discharging of a series RC circuit of a module induces the charging or discharging of the series RC circuit of the next module;
- each module includes:
   a first transistor the source whereof is connected to the input of the module, the gate to the output thereof and the drain to the gate of the associated switch,
   a first inverter the input whereof is connected to that of the module and the output to a first terminal of the resistor of the series RC circuit, the second terminal of the resistor being connected to a first terminal of the capacitor, the second terminal thereof being connected to the ground,
   a second inverter the input whereof is connected to the second terminal of the resistor and the output to that of the of the module, said output forming the input of the next module.
- each module includes:
   a first transistor the gate whereof is connected to the input of the module and the drain to the positive power supply terminal;
   a second transistor the source whereof is connected to that of the first transistor, the gate to the output of the module and the drain to a first terminal of the variable-impedance sensor the second terminal whereof is connected to the ground,
   a diode the anode whereof is connected to the source of the first transistor and the cathode to a first terminal of the resistor of the series RC circuit, the second terminal thereof being connected to the output of the module, the capacitor of the series RC circuit being connected between the output of the module and the ground.
- each set of a switch and a sensor is mounted in series and the sets of a switch and a sensor are mounted in parallel with respect to one another;
- each set of a switch and a sensor is mounted in parallel and the sets of a switch and a sensor are mounted in series with respect to one another; the electrical power source includes a current-conducting surface of the medical device, suitable for inducing an electrical current under the effect of an electromagnetic field;
- at least one of the sensors is arranged on a surface of the medical device, intended to be in contact with a part of the body whereon the device is applied or wherein the device is implantable;
- the antenna is formed by a part at least of the medical device;
- the measurement circuit includes a plurality of fixed impedances, each associated with a switch the opening and closing whereof are controlled by the control system; the medical device is implantable in the human body and is chosen from the group comprising:
   a vascular support or stent, at least one sensor being preferably arranged on an abluminal surface of the vascular stent,
   a heart valve,
   a cardiac stimulator,
   a cochlear implant,
   a throat implant,
   an orthopaedic implant,
   a brain implant,
   a retinal implant,
   a catheter, or
   a cellular tissue;
- each sensor is chosen from:
   a shear sensor,
   a pressure sensor,
   an impedance sensor,
   a heat dissipation sensor,
   a stress gauge, and
   a flow sensor, particularly of the hot-wire type;
- the implantable medical device is a vascular stent with at least one impedance sensor arranged on an abluminal surface of the vascular stent;

the medical device forms a through conduit, the medical device including two pressure sensors arranged at each of the ends of the through conduit, in the through conduit;

the medical device comprises between two sensors each associated with a switch, an element of fixed and known impedance being preferably provided between each of the sets of a sensor associated with a switch;

the medical device is a meshed vascular stent, at least one sensor, preferably all the sensors, being arranged at the mid-point of one side of a mesh of the vascular stent;

the medical device comprises at least one analogue/digital converter, the output signal whereof controls the emitting antenna, optionally indirectly, particularly via a variable resistor; and the medical device comprises a plurality of measurement lines, the measurement lines extending on the medical device, particularly on the vascular stent, along coaxial helices.

The invention also relates to a medical system comprising a medical device as described above in any combinations thereof and a unit for receiving information from the medical device, comprising means for sensing the electromagnetic field emitted by the antenna of the medical device.

The medical system may further comprise a unit for querying the medical device, preferably merged with the unit for receiving information, preferably comprising means for emitting an electromagnetic field suitable for creating an induced current in the measurement circuit of the medical device.

The medical system may comprise a comparator intended to compare an identifier emitted by the querying unit, with a binary code associated with a given combination of fixed impedances of the measurement circuit of the medical device.

The medical system may further comprise a unit for processing the information received by the reception unit, for example a computer, the unit for processing information preferably having a screen to display in real time a model of the medical device whereon is transferred information relating to the values of the measurements made using the sensors.

The invention also relates to a method for querying a medical device as described above in any combinations thereof, particularly in a medical system as described above in any combinations thereof, comprising steps consisting of:

powering the measurement circuit of the medical device, activating the control system so that it successively controls the opening or closing of each of the switches, according to determined configurations, and measuring the electromagnetic field emitted by the antenna of the medical device.

The method may comprise a step for identifying the medical device.

The method may also comprise a calibration step prior to each measurement or prior to certain measurements of the magnetic field emitted by the antenna of the medical device, corresponding to the magnetic field emitted by the antenna according to the current passing through the impedances and/or the elements of fixed and known impedance.

The appended figures will help understand clearly how the invention may be embodied. In these figures, identical references denote similar elements.

Hereinafter in the description, elements that are identical or have an identical function bear the same reference sign in the various embodiments. For the purposes of conciseness of the present description, these elements are not described with regard to each of the embodiments, only the differences between the embodiments being described.

Figure 1:
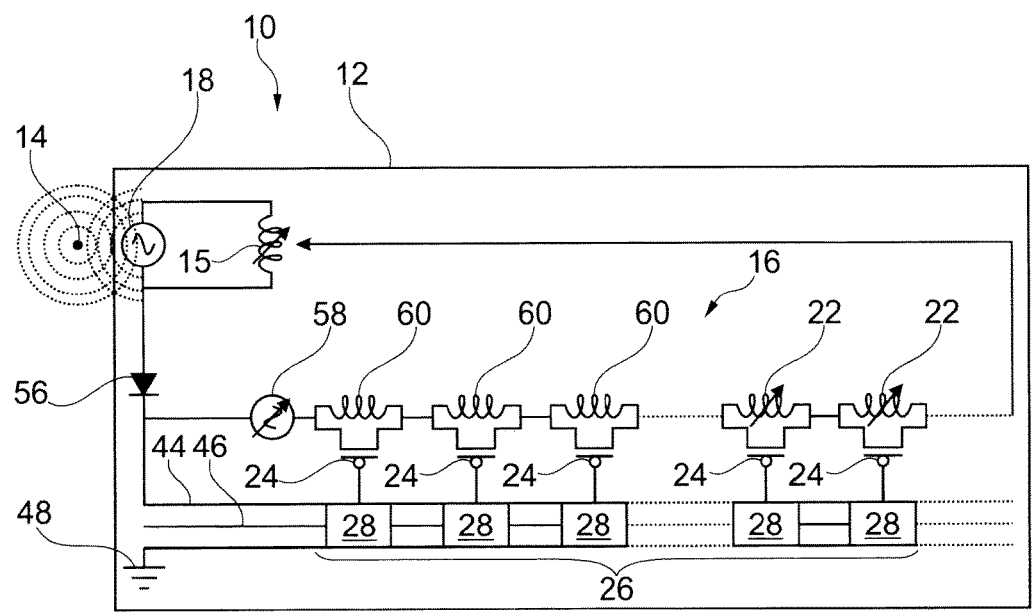
FIG. 1 represents schematically a first example of a medical system comprising a medical device.

FIG. 1 illustrates schematically a medical system 10 comprising an implantable medical device 12 and a unit 14, herein single, for querying the medical device 12 and receiving information from said medical device 12. Obviously, units for querying and receiving information may, alternatively, be separate. The medical device 10 may further comprise a unit for processing the information received by the receiving unit, for example a computer.

The implantable medical device 12 includes a variable impedance 15. The value of this variable impedance 15 is controlled by a control unit not shown, according to the impedance in a measurement circuit 16, connecting particularly the various sensors 22 of the implantable medical device. The implantable medical device 12 further includes an electrical power source, herein a source of electric current formed by the body 18 of the implantable medical device 12. Indeed, under the effect of an electromagnetic field emitted by the querying unit 14, the body 18 of the implantable medical device 12 induces a current. Alternatively, an antenna or armature separate and electrically insulated from the body 18 of the implantable medical device 12 may also be provided, particularly in the case wherein the implantable medical device 12 is not suitable, completely or partially, for having an armature function. In the latter case in particular, an electrical power source for the measurement circuit may include a current-conducting surface of the implantable medical device, suitable for inducing an electric current under the effect of an electromagnetic field. An electric battery or cell may also be provided as an electrical power source for the implantable medical device 12.

The body 18 of the implantable medical device 12 serves herein also as an emitting antenna, to emit an electromagnetic field outside the body wherein the implantable medical device is implanted. For example, at a constant induced current intensity of the electrical power source, the intensity of this field is directly dependent on the variable impedance 15, according to the impedance in the measurement circuit 16. As such, the intensity or a standard of the electromagnetic field emitted by the body 18 of the implantable medical device 12 (or more generally of the emitting antenna) is dependent on the impedance of the measurement circuit 16.

Alternatively, the implantable medical device 12 may include an antenna separate from the body of the implantable medical device or the antenna may be formed by a part at least of the implantable medical device.

The implantable medical device 12 is for example a stent. The stent is a tubular metal device, preferably meshed, inserted into a natural human (or animal) cavity to keep it open, as described above in the introduction. The stent may for example be made of a metal alloy or polymer material, but other materials may also be envisaged.

The implantable medical device 12 is provided with variable-impedance sensors 22 according to the physical quantity detected thereby. The term physical quantity denotes herein any property of natural science which may be quantified by measurement or computation, and the different possible values whereof are expressed using any real number or a complex number. A physical quantity includes therefore, for example, a length, an electric current, a voltage, an impedance, a concentration of a chemical element or even the presence and/or concentration of a biological or biochemical element.

The sensors 22 are distributed on the surface of the implantable medical device. In the particular case of the stent described herein, the sensors 22 may particularly be distributed:
- only on the "abluminal" surface of the body of the stent, i.e. the surface opposite the lumen through the stent, intended to be in contact with the wall of the cavity to be kept open but not on the luminal surface; or
- only on the luminal surface but not on the abluminal surface; or
- both on the luminal and abluminal surfaces; and
- on the surfaces connecting the luminal and abluminal surfaces.

The sensors may be coated with an active agent, for example to limit hyperplasia of the tissues in contact with the implantable medical device, particularly when they are positioned on the abluminal surface of a stent or more generally on the outer surface of an implantable medical device intended to be in contact with the wall of the cavity wherein the medical device is implantable.

It should be noted that positioning a single sensor, particularly a pressure sensor, on the abluminal surface of a stent, or more generally on the outer surface of an implantable medical device already makes it possible to obtain information relating to the poor positioning of the stent or implantable medical device in the cavity. If the pressure measured is low (i.e. less than a threshold pressure), it is likely that the sensor is not in contact with a wall of the cavity, but rather with blood, for example. In the case where two sensors or more are arranged on the abluminal or outer surface, the information may be obtained with more precision by comparing the values measured by the sensors with one another.

Figure 13:
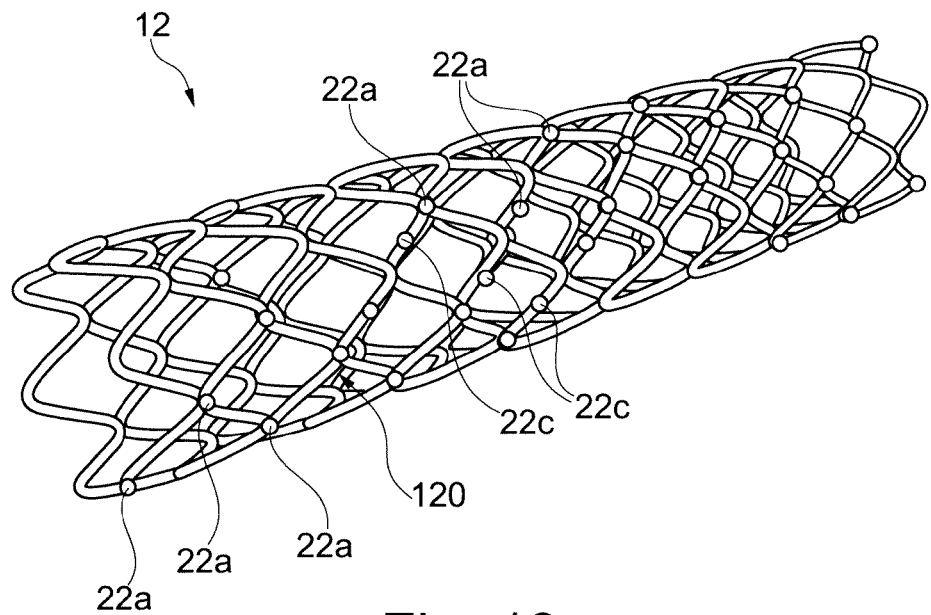
FIG. 13 represents schematically in perspective a stent provided with sensors.

Preferably, the sensors are arranged at the locations of the implantable medical device, particularly a stent, subject to the least deformations during the fitting of the implantable medical device, in order to avoid damaging the sensors. As such, although FIG. 13 shows a stent 12 with sensors 22a fixed to the vertices of the meshes 120 of the stent 12 and sensors 22c fixed to the mid-point of the sides of the meshes of the stent, it is preferred that all the stents 22c be fixed to the centre of sides of the meshes 120 of the stent 12. The sensors 22a, 22c may be arranged on the inner face or on the outer face of the stent 12. However, it is particularly advantageous to place a pressure sensor in the vicinity of each end of the stent 12, on the inner face of the stent. As such, a difference in pressure between the values measured by these two sensors may be determined which makes it possible to identify the appearance of a blockage inside the stent.

Each of the sensors may particularly be chosen from:
- a shear sensor,
- a pressure sensor,
- an impedance sensor,
- a heat dissipation sensor,
- a stress gauge, and
- a flow sensor of the "hot wire sensor" type.

The sensors 22 are variable-impedance sensors, i.e. sensors wherein the impedance varies according to the amplitude or intensity of the physical quantity detected. Hence, in the event of variation of the amplitude of the physical quantity detected by a sensors of the implantable medical device 12, the impedance of this sensor varies in the measurement circuit 16, such that, in the absence of any other variation in the measurement circuit 16, the impedance of the measurement circuit 16 also varies.

As illustrated, each sensor 22 is associated with a switch 24 suitable for disconnecting from the circuit, in this instance short-circuiting, the sensor 22 with which it is associated. Herein, this is carried out by mounting the switch 24 in derivation (or in parallel) with the sensor 22 with which it is associated. The sensors 22 are herein mounted in series in the measurement circuit 16. For reasons of ease of embodiment and miniaturisation, each switch is herein embodied by a transistor 24, in this instance a silicon MOS-FET transistor, more specifically a depletion-mode, P-channel MOS-FET (or p-MOS) transistor. In further embodiments, each switch or certain switches may be embodied by another type of transistor, particularly by a FET transistor, an enhancement-mode MOS-FET transistor, particularly an enhancement-mode N-channel MOS-FET transistor, by a MEMS (standing for "Micromechanical system"), or by a mechanical switch.

FIG. 1 further illustrates a system 26 for controlling the switches 24, suitable for successively controlling the opening or closing of the switches 24 according to determined configurations. Herein, the control system 26 includes control modules 28 arranged in series with one another, each control module 28 being suitable for controlling the opening or closing of the switch 24 with which it is associated.

In this instance, the control system 26 is configured to normally keep the switches 24 closed and to open same successively and then to close them again such that, at each time, a single switch 24 is open.

For this purpose, each control module 28 is formed herein of a logic circuit, embodied by means of transistors 30, 32, 34, 36, 38, a resistor 40 and a capacitor 42. The resistor 40 and the capacitor 42 introduce a charging time of the capacitor 42 and a discharging time of said capacitor 42 in the logic circuit. During these charging and discharging times, the control module 28 controls the opening of the associated switch 24. The switch 24 is kept closed for the rest of the time, thereby short-circuiting the associated sensor 22.

Figure 2:
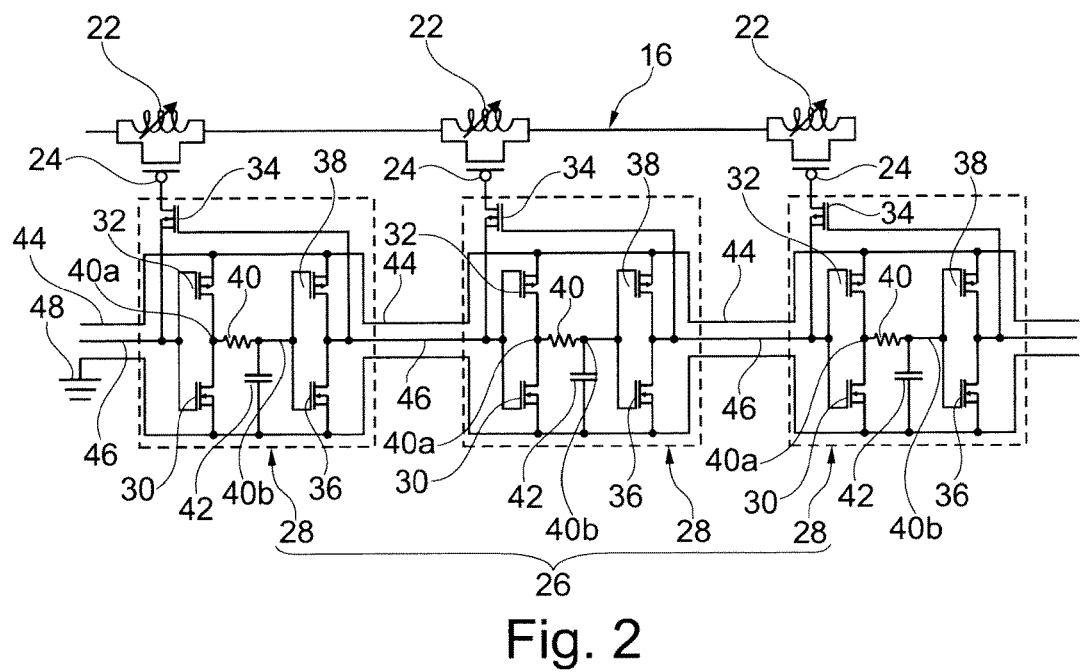
FIG. 2 represents schematically a detail of the electrical circuit of the stent in FIG. 1.

More specifically, and as shown in FIG. 2, herein, each control module 28 is embodied by means of three P-channel transistors 32, 34, 38 and two N-channel transistors 30, 36, as follows (only the connections hereinafter are made);
first and second branches 44, 46 of the measurement circuit 16 are connected in parallel, the first branch 44 being the positive power supply terminal and the second branch 46 being the input of the measurement circuit 16 which is powered by a start circuit, not shown in the figures, configured to generate a crenelated voltage pulse during a certain time interval;

the gate of the first transistor 30 and the gate of the second transistor 32 are connected together, as well as to the source of the third transistor 34 and to the second branch 46 of the preceding control module 28, the two transistors 30 and 32 forming a first inverter;

the gate of the fourth transistor 36 and the gate of the fifth transistor 38 are connected together as well as to a terminal of the resistor 40 and to a terminal of the capacitor 42, the two transistors 36 and 38 forming a second inverter;

the source of the first transistor 30, the source of the fourth transistor 36 and a terminal of the capacitor 42 are connected to the ground 48;

the other terminal of the resistor 40, which is not connected to the capacitor 42, is connected to the drain of the first transistor 30 and to the drain of the second transistor 32;

the drain of the fourth transistor 36 and the drain of the fifth transistor 38 are connected together to the second branch 46 of the next control module 28, as well as the gate of the third transistor 34;

the source of the second transistor 32 and the source of the fifth transistor 38 are connected together to the first branch 44 of the preceding control module 28;

the drain of the third transistor 34 is connected to the gate of the transistor 24 having a switch function to short-circuit the sensor 22.

When the voltage applied at the input of the first inverter is close to zero, therefore less than the threshold voltage of the transistors 30 and 32, the PMOS type transistor 32 is switched to the ON-state, charging the capacitor 42. At the end of the charging thereof, the voltage at the input of the second inverter is greater than the threshold voltage of the transistors 36 and 38, rendering the NMOS type transistor 36 ON. A voltage close to zero is transmitted at the output of the second inverter connected to the gate of the PMOS type transistor 34. The latter is then switched to the ON-state, transmitting a voltage close to zero to the gate of the PMOS type switch 24, which triggers the closing thereof. While a voltage close to zero is applied to the input of the first inverter, the switch 24 is kept closed.

When a voltage greater than the threshold voltage of the transistors 30 and 32 is applied at the input of the first inverter, the NMOS type transistor 30 is switched to the ON-state, transmitting to the output thereof the ground potential, which triggers the discharging of the capacitor 42. During this discharging, the voltage at the input of the second inverter decreases until it becomes less than the threshold voltage of the transistors 36 and 38, inhibiting the transistor 36 and activating the transistor 38. The latter thereby transmits to the output of the second inverter a potential greater than the threshold voltage of the transistor 34, triggering the inhibition thereof. Consequently, the switch 24 opens. As such, by applying a high positive voltage at the input of the first inverter of the first control module 28, the opening is induced of the switch 24 which is connected thereto, followed by the successive opening of the switches 24 connected to the subsequent control modules 28. The start circuit, not shown, powering the input 46 of the first module is configured to generate a crenelated voltage pulse for a time interval $\tau=RC$. The trailing edge of this pulse induces the closing of the switch of the first module after a time equal to $\tau$. The voltage pulse is propagated from one input 46 to another, such that the trailing edge of this pulse at the input of a module n corresponds to the leading edge of the pulse at the input of the module n+1. As such, in this instance, during the propagation of the pulse, all the switches are closed except one.

With such a control system, the voltage at the terminals of the measurement circuit 16, which is equal to the sum of the voltages at the terminals of each of the sensors mounted in series in the measurement circuit, exhibits successive peaks which are representative of the voltage at the terminals of each of the sensors. To each of the successive peaks, each representative of the voltage at the terminals of a sensor 22, corresponds an intensity of the electromagnetic fields emitted by the body 18 of the implantable medical device 12 having an emitting antenna function.

In FIG. 1, the presence of a rectifier 56 as well as of an alternating current generator 58 in the implantable medical device 12 is observed. They make it possible respectively to supply the control circuit 26 with direct current and the measurement circuit 16 with a current having a frequency distinct from, particularly less than, the frequency of the induced current in the antenna 18. This may be useful as the frequency of the induced current is dependent on the electromagnetic field emitted by the unit 14 said frequency being preferably chosen such that the electromagnetic wave is absorbed to a low degree by the tissues traversed. The use of such a frequency in the measurement circuit could impede the precision of the measurements made.

The measurement circuit 16 is moreover completed in FIG. 1, by a combination of sets of an impedance 60, that is fixed and known, and a switch 24, controlled by a control module 28, as is the case for the switches 24 associated with the sensors 22. This combination of known impedances makes it possible to identify the implantable medical device queried, for example by associating a combination of impedances 60 that are unique and known to each implantable medical device 12. This particularly useful in the case where a plurality of such implantable medical devices have been implanted in the body of the same patient. Some electromagnetic field peaks measured are then used to identify the implantable medical device 12, the other peaks to determine the values measured by each of the sensors of the implantable medical device 12 identified. For example, the first electromagnetic field peaks measured may be used for identifying the implantable medical device 12 and the subsequent peaks for determining the values measured by each of the sensors of the implantable medical device 12 identified. Furthermore, these impedances being known, they are also suitable for calibrating the medical system 10. In other words, these known impedances make it possible to quantify more accurately the values measured by the different sensors of the different implantable medical devices.

Figure 15:
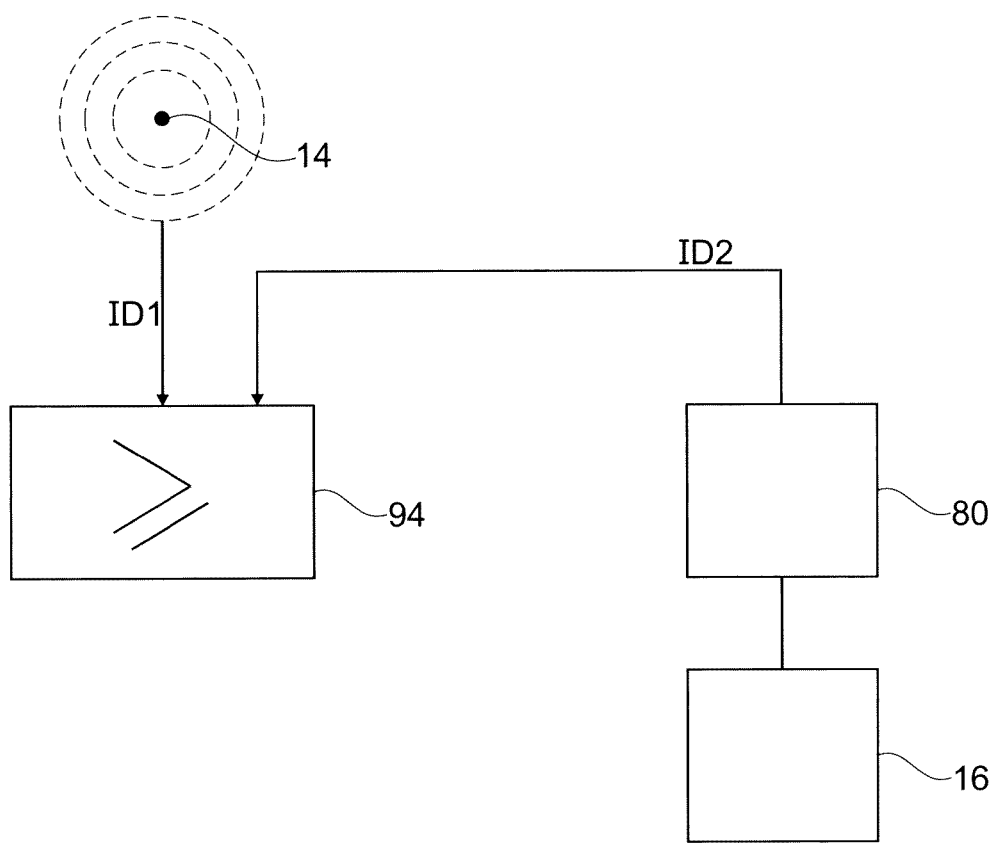
FIG. 15 represents schematically a medical device identifier comparator.

Alternatively, according to the embodiment represented partially and schematically in FIG. 15, the medical device may include a comparator 94 for comparing an identifier ID1 emitted by the querying unit 14, with a binary code ID2 associated with the combination of impedances 60 present on the electrical circuit, this binary code being derived for example from the output of the analogue/digital converter 80, or an identifier saved in a memory in the stent. The medical device may then be configured to only respond to the query by the querying unit if the comparison is positive. Advantageously, the identification may be carried out iteratively, the querying unit merely emitting one identification value at a time, each stent wherein the value corresponding of the identifier not corresponding being disabled—i.e., herein, not electrically powered—for a time suitable for identifying the only stent corresponding to the unique identifier and carrying out the measurements using different sensors in this medical device.

Figure 3:
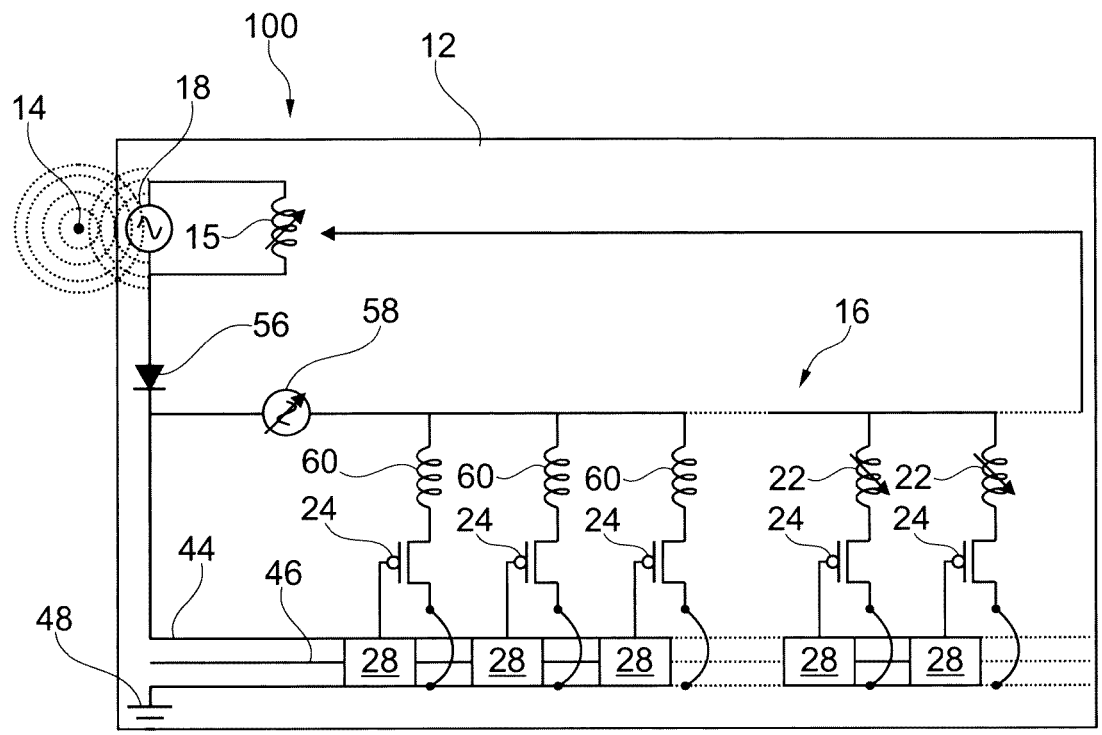
FIG. 3 represents schematically a second example of a medical system comprising a medical device.

FIG. 3 represents a second example of a medical system 100. This medical system is substantially identical to that described above. However, in this embodiment, in the measurement circuit 16 of the implantable medical device 12, the known impedances 60 and the sensors are mounted in series with the switch 24 which is associated therewith, the sets formed of an impedance 60 or a sensor 22 and a switch 24 being mounted in parallel (or in derivation) with respect to one another. Hence, the control modules 28 being identical to those described above, the electromagnetic field emitted following the creation of an induced current, corresponds to the sum of all the impedances 60 and of all the sensors 22, minus one, each of the impedances 60 and the sensors 22 being disconnected from the circuit, in this instance disconnected, successively.

Alternatively, obviously, it is possible to embody a control module 28 having a different operation, which controls the closing of the switch 24 during a time interval only, the switch 24 being open the rest of the time. Such an operation may also be obtained by retaining the control module 28 as described above and by replacing the depletion-mode MOS-FET transistors used as switches 24 by enhancement-mode MOS-FET transistors.

Figure 4:
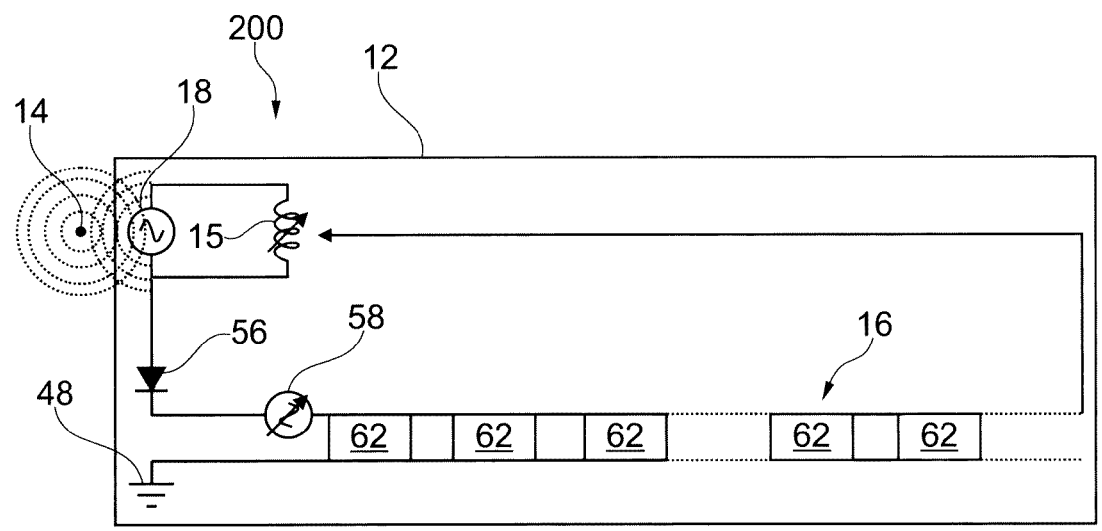
FIG. 4 represents schematically a third example of a medical system comprising a medical device.
Figure 5:
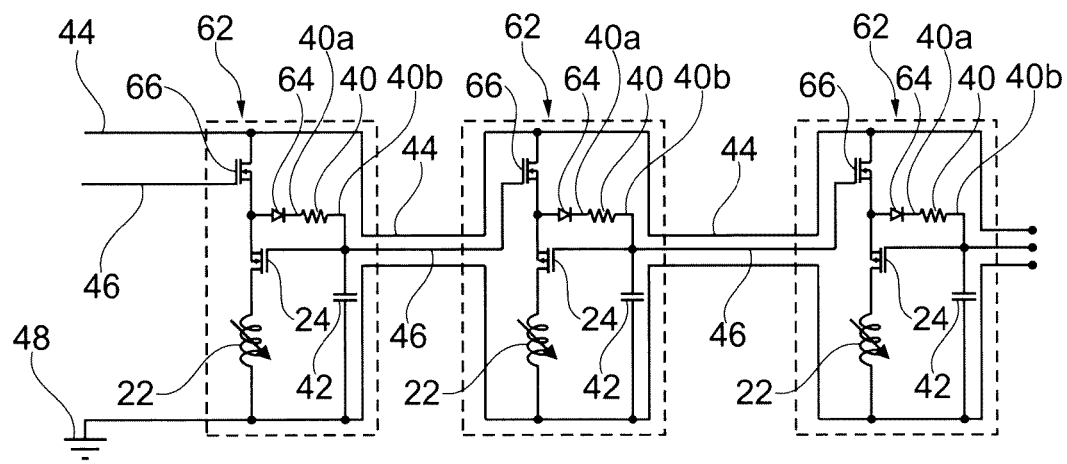
FIG. 5 shows schematically a detail of the medical device in FIG. 4.

FIGS. 4 and 5 illustrate a further example of a medical system 200. According to this example, the control of the switch 24 for disconnecting from the circuit the sensor 22 or a known impedance 60 is implanted directly in a module 62 also comprising the known impedance 60 or the sensor 22, and the switch 24, herein embodied by a transistor. As for the other examples described above, a resistor 40 and a capacitor 42 are used to control the switch 24 such that it disconnects from the circuit the impedance 60 or the sensor 22 except during a charging time interval of the capacitor 42. Charging the capacitor 42 activates the transistor 66 of the next module, inducing the charging of the corresponding capacitor 42. Once charged, the capacitor 42 inhibits the associated transistor 24, triggering the disconnection from the circuit of the impedance 60 or the sensor 22 which is connected thereto.

Herein, as represented in FIG. 5, each module 62 is embodied as following:
- the first and second branches 44, 46 are in parallel;
- a terminal of the sensor 22 or of the impedance 60 is connected to the ground 48;
- the other terminal of the sensor 22 or of the impedance 60 is connected to the drain of the transistor 24;
- the gate of the second transistors 66 is connected to the second branch 46 of the preceding module 62;
- the drain of the second transistor 66 is connected to the first branch 44 of the preceding and next modules 62;
- the source of the second transistor 66 is connected to the source of the transistor 24 and to a diode 64;
- the other terminal of the diode 64, which is not connected to the transistors 24, 66, is connected to a terminal of a fixed impedance 40;
- the other terminal of the impedance 40, which is not connected to the diode 64, is connected to the gate of the transistor 24, to a terminal of a capacitor 42, connected by the other terminal thereof to the ground 48, and to the second branch 46 of the next module 62.

As for the preceding examples, due to the configuration of the modules 62, each sensor 22 and impedance 66 is successively connected to the antenna 18 in order to be powered, the other sensors 22 and impedances 66 being for their part disconnected.

Figure 6:
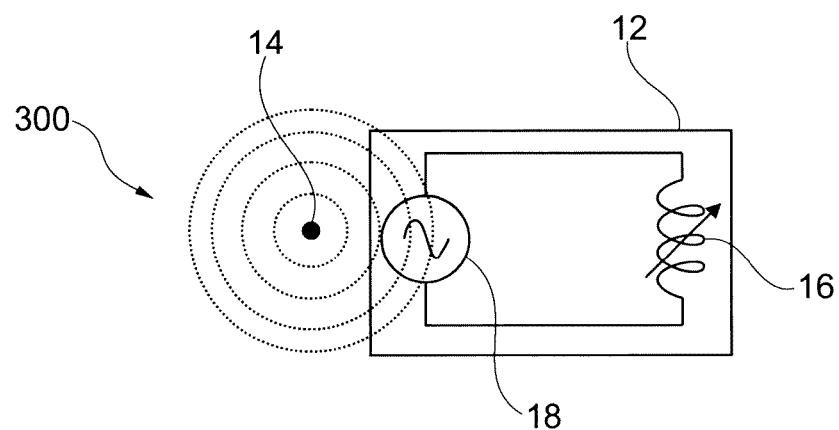
FIG. 6 represents schematically a fourth example of a medical system comprising a medical device.

Finally, FIG. 6 represents a fourth example of an embodiment of a medical system 300. This medical system 300 is distinguished from the preceding example 200, in that the measurement circuit 16 is directly connected to the antenna 18 for the emission of an electromagnetic field, without the intermediary of a separate variable impedance (the measurement circuit 16 itself having a variable impedance) and of a unit for controlling this variable impedance according to the impedance of the measurement circuit 16. The electrical circuit on the medical device 12 is then particularly simplified.

Obviously, it is possible to conceive a structure where the measurement circuit 16 is connected directly to the antenna, the implantable medical device also comprising a control circuit associated with this measurement circuit and as described for example with regard to FIGS. 2 and 3.

In practice, in the embodiments described above, each module may particularly by embodied in the following form. Two measurement electrodes, for example of 60×60 $\mu m^2$, made of an electrically conductive material, for example of polymer material or of metal alloy, preferably biocompatible, are deposited on an electrically insulating, biocompatible polymeric substrate (for example parylene). The electrical components of the control system and the switch are implanted in the polymeric substrate.

Figure 14:
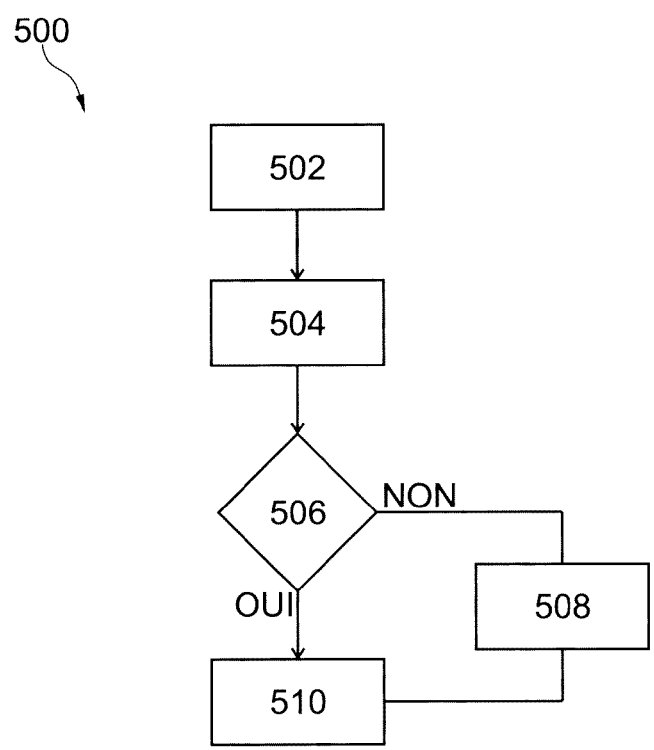
FIG. 14 is a flow chart of a method for querying a medical device.

The medical systems described above are suitable for carrying out a querying method 500 of the implantable medical device 12, as shown by the flow chart in FIG. 14.

This method 500 includes a first step 502 consisting of powering the measurement circuit 16. Preferably, this power supply is carried out by an induced current in an antenna or in the body of the implantable medical device 12 when the latter is configured to generate an induced current. This makes it possible to power the measurement circuit 16 only when a measurement is made.

The method 500 is continued by a step 504 consisting of activating the system for controlling the implantable medical device so that it successively controls the opening of the closing of each of the switches of the implantable medical device, according to determined configurations. It should be noted herein that within the scope of the examples described with regard to the figures, this activation is carried out simultaneously with the power supply of the measurement circuit 16, by induction, in response to the emission of an electromagnetic field by the querying device. The method 500 then includes a step 506 for identifying the queried medical device. This step may, alternatively, be carried out before electrically powering the measurement circuit.

The identification may be carried out either in the medical device per se, when the latter is provided with a comparator to compare an identification signal emitted by the querying unit with a unique identifier of the medical device. As indicated above, this identifier may take the form of a combination of known impedances in the medical device and/or in each measurement line of the medical device. The identification may be carried out iteratively, the querying unit merely emitting one digit of the identifier at a time, each of the medical devices wherein the identifier does not correspond to this digit being temporarily deactivated (i.e., in the example studied, not electrically powered).

Alternatively, the identification is carried out in the processing unit, the signals emitted by the antenna 18 being interpreted by the processing unit to determine the combination of the impedances of the medical device and/or of the measurement line queried. A processing unit may be used to determine the value measured by each sensor and the implantable medical device that responded to the query, particularly if the controlled configurations of the measurement circuit are more complex.

To do this, the processing unit may particularly be suitable for conducting Fourier analyses of the measured signals of electromagnetic fields emitted by the antenna of the implantable medical device, comparing the signals received (optionally processed) to previously measured signals and inferring therefrom the values measured by the various sensors of the implantable medical device, one location being suitable for being determined for each of the values measured.

If the identification is negative, the medical device is temporarily deactivated, in the step 508.

If the identification is positive, the method 500 is continued then by a step 510 consisting of measuring the electromagnetic field emitted by the antenna of the implantable medical device. This measurement is made over a relatively long time so that the control system will have been able to control a relatively large number of different configurations of the measurement circuit so that the measurement makes it possible to determine the value measured by each of the sensors 22 of the implantable medical device 12. Throughout the measurement step, the antenna 14 preferably emits a constant electromagnetic field to maintain the power supply of the measurement circuit 16 and the activation of the control system 26.

Preferably, each configuration corresponds to the scenario where all the sensors or impedances of the measurement circuit are disconnected from the circuit, except one. As such, on the basis of the electromagnetic field measured, it is possible to determine first of all the implantable medical device that responded to the query. Indeed, the first peaks measured in the electromagnetic field emitted by the antenna correspond to fixed impedances, the combination whereof makes it possible to identify the implantable medical device. These magnetic fields measured may also be suitable for calibrating the system since the magnetic fields measured correspond to known impedances of the measurement circuit. Finally, the subsequent magnetic fields make it possible to determine the values measured by each of the sensors distributed on the implantable medical device.

When elements 60A are envisaged between the sensors 22, the corresponding magnetic fields emitted may be used to calibrate the following and/or preceding emitted signal, which originates from a measurement by a sensor 22.

Once all the sensors 22 of the medical device 12 have been queried, the electrical power supply of the electrical circuit is switched off and the electrical circuit of the medical device 12 is deactivated.

It should be noted herein that the method described may be used with any type of variable-impedance sensor according to the physical quantity detected thereby. It should also be noted that the sensors distributed on the implantable medical device may be of different types, i.e. they may detect different physical quantities.

The method described above may particularly be used to determine whether the implantable medical device is suitably implanted (i.e. positioned) in the natural cavity that it is supposed to keep open, in particular, if it is indeed in contact with the wall of the cavity. Indeed, the effect of a stent, for example but this is true for most implantable medical devices, is markedly reduced if the latter is not bearing on the wall of the cavity (particularly of the vein or the artery) wherein it is inserted.

For example, by placing pressure sensors on the abluminal surface of the stent, i.e. on the surface opposite the lumen through the stent, that which is intended to be in contact with the wall of the cavity wherein the implantable medical device is received, the method described above makes it possible to determine whether each of these sensors is in contact with the wall, since it makes it possible to determine the pressure measured by each of the sensors. Obviously, this function for determining the suitable position of the stent may be combined, that is to say that sensors, for example of pressure, may be arranged on the abluminal surface of the stent and sensors, optionally of another physical quantity, may be arranged on the luminal surface of the stent.

Alternatively, sensors of the same physical quantity are distributed on the abluminal surface and on the luminal surface, substantially at the same position on the stent or implantable medical device. In other words, sensors of the same physical quantity are arranged at the same point of the stent, on either side of the stent body. The comparison of the values measured by each of these stent pairs also makes it possible to obtain indications of an incorrect position of the stent in the cavity. In particular if the sensor on the abluminal surface, which should therefore be in contact with a wall, measures a substantially identical value to the sensor on the luminal surface, which is in contact with the blood, it is likely that the sensor on the abluminal surface is in fact in contact with blood also, not with a wall. It is therefore likely that the stent is poorly positioned in the cavity.

Obviously, the method described above may be suitable for obtaining numerous other items of information.

In particular, it may be suitable for determining whether a sensor arranged on the luminal or abluminal surface of the stent or, more generally, on a surface of an implantable medical device, particularly on a surface of the implantable medical device in contact with a wall of the cavity wherein the medical device is implanted or on a surface of the implantable medical device intended to be in contact with the blood, is optionally coated with endothelial or smooth muscle tissue.

It may also be suitable for determining the composition of the tissue coating the sensors distributed on the implantable medical device (particularly on the luminal surface or on the abluminal surface of a stent) for example by Electrical Impedance Spectroscopy (EIS), particularly by applying currents of separate frequencies in the measurement circuit.

Figure 7:
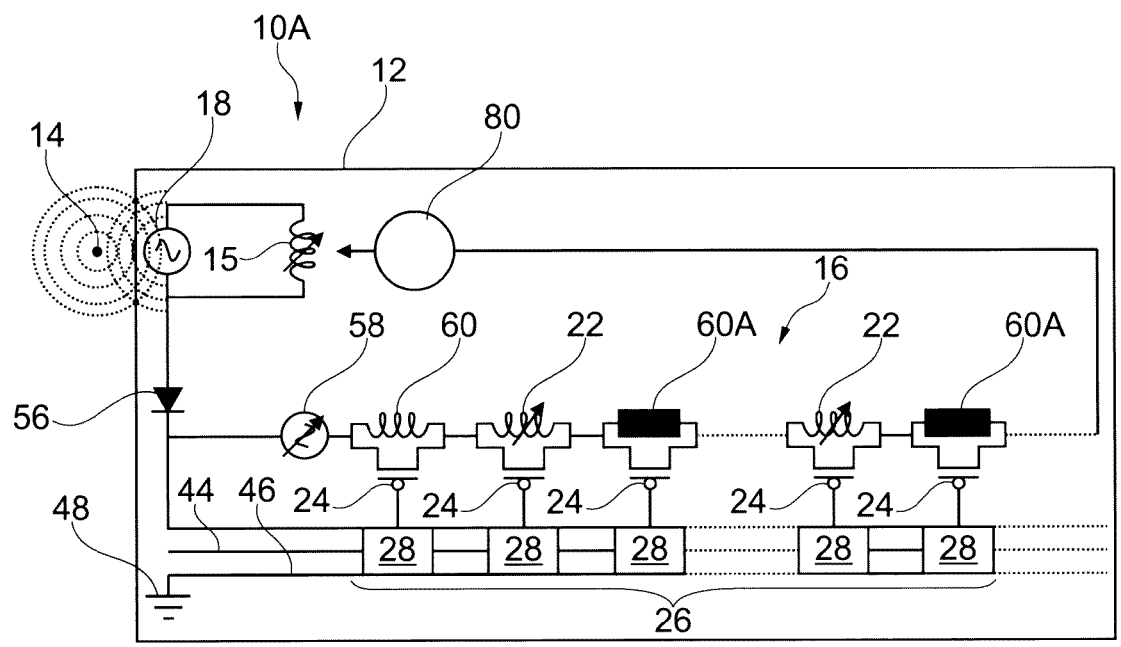
FIGS. 7 and 8 are schematic representations of alternative embodiments of the electrical circuits in FIGS. 1 and 3.

The electrical circuit 10A in FIG. 7 is an alternative embodiment of the circuit in FIG. 1.

The electrical circuit 10A firstly includes an analogue/digital converter 80 situated between the electrical measurement circuit 16 and the variable impedance 15 connected to the antenna 18 in the emitting circuit. This analogue/digital converter 80, which may also be used in the electrical circuit 10 in FIG. 1 makes it possible to increase the range of signals which may be emitted by the antenna 18. This converter 80 also makes it possible to enhance the signal-to-noise ratio of the measurements made.

Moreover, the electrical circuit 10A is distinguished from that in FIG. 1 by the presence of an element 60A of fixed and known impedance, for example a resistor, between the sensors 22. As for the impedances 60, the element 60A is associated with a switch 24 controlled by a control module 28 in a module 62A. The impedance of this element 60A is preferably chosen such that the sensors 22 cannot attain this impedance value. For example, the impedance of the element 60A is less than 90% of the minimum impedance suitable for being attained by sensor 22 and/or greater than 110% of the maximum impedance suitable for being attained by a sensor 22. As such, between two emitted signals relative to a measurement by a sensor 22, a transition signal, easily identifiable, is emitted. It is easier, as such, to distinguish between two successive measurements, separated by a signal of expected form. Moreover, the presence of this element 60A between the sensors 22 may be suitable for calibrating the following and/or preceding sensor 22. The measurement is therefore more precise. Obviously, further configurations may be envisaged. In particular, it is possible to envisage an element 60A at the start of a line only, all the n sensors 22, n being a natural integer different to zero, or even an irregular distribution of the elements 60A on the measurement line.

Figure 8:
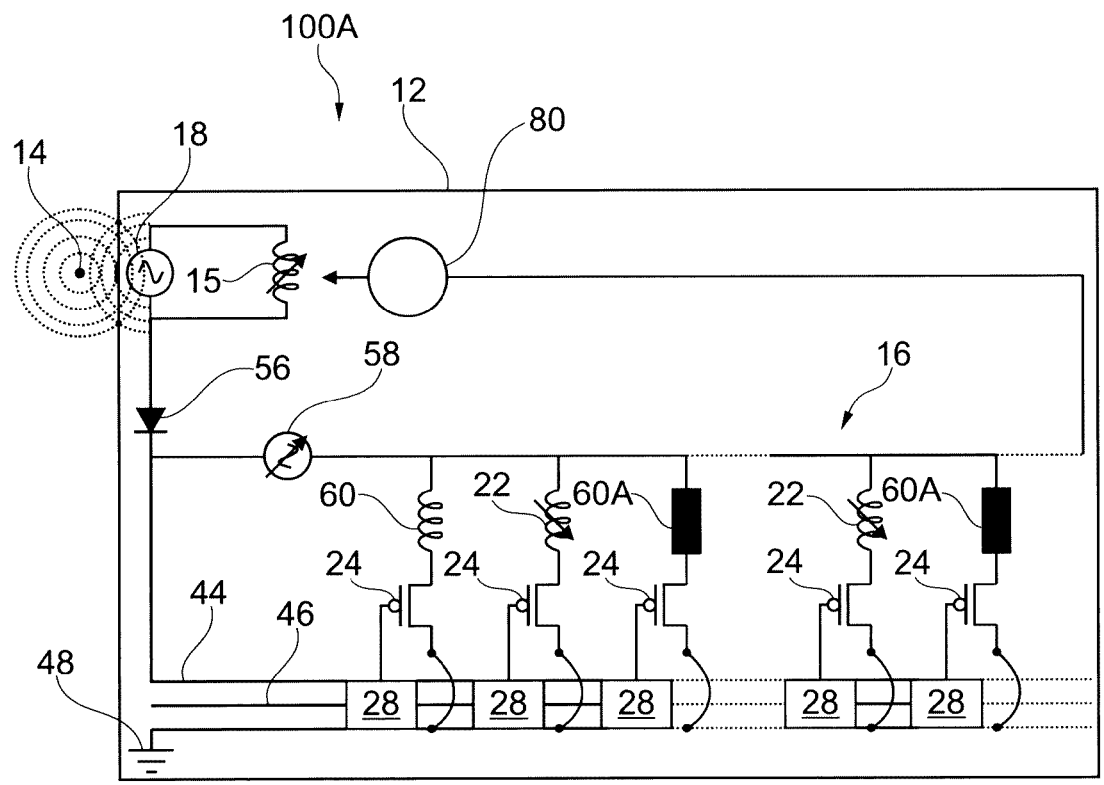

FIG. 8 represents an alternative embodiment 100A of the electrical circuit 100 in FIG. 3, with an analogue/digital converter 80 and elements 60A of known and fixed impedance, such as the electrical circuit 10A. The advantages of these modifications are the same as within the scope of the electrical circuit 10A in FIG. 7.

Figure 9:
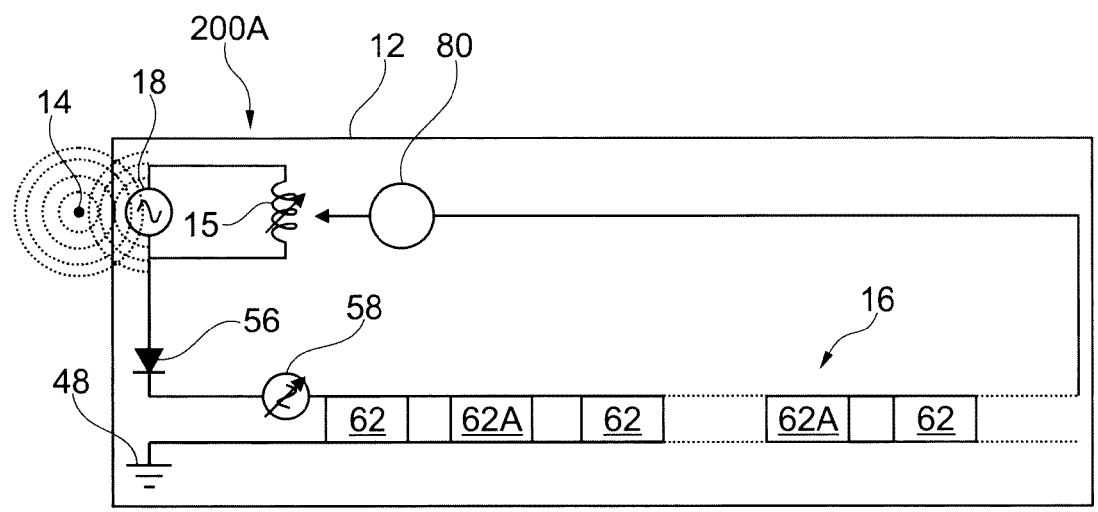
FIGS. 9 and 10 illustrate schematically an alternative embodiment of the electrical circuit in FIGS. 4 and 5.
Figure 10:
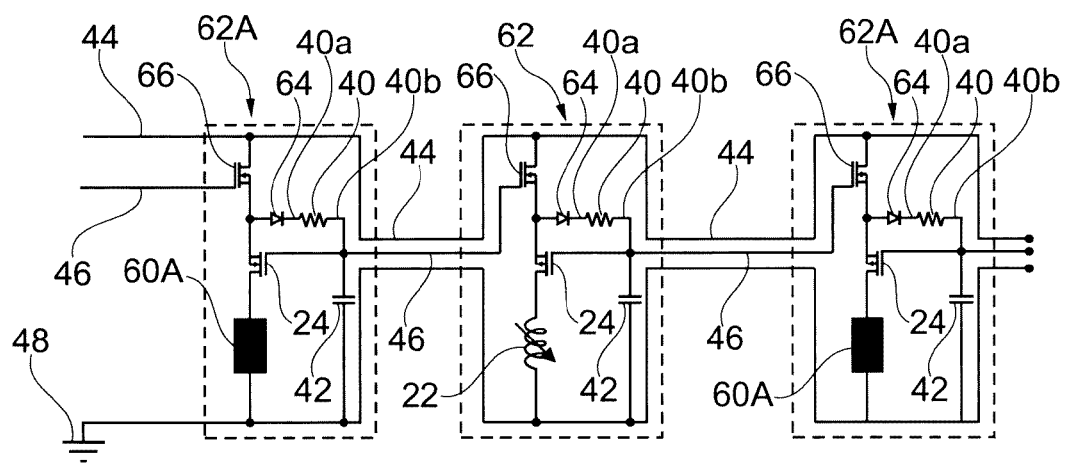

The same applies for the electrical circuit 200A illustrated by FIGS. 9 and 10 and obtained by making the same modifications to the electrical circuit 200 in FIGS. 4 and 5.

It should be noted herein that the presence of the elements 60A of known and fixed impedance and of the analogue/digital converter 80 are independent. Embodiments may be envisaged not involving one of the two among the analogue/digital converter 80 and the elements 60A of known impedance.

Figure 11:
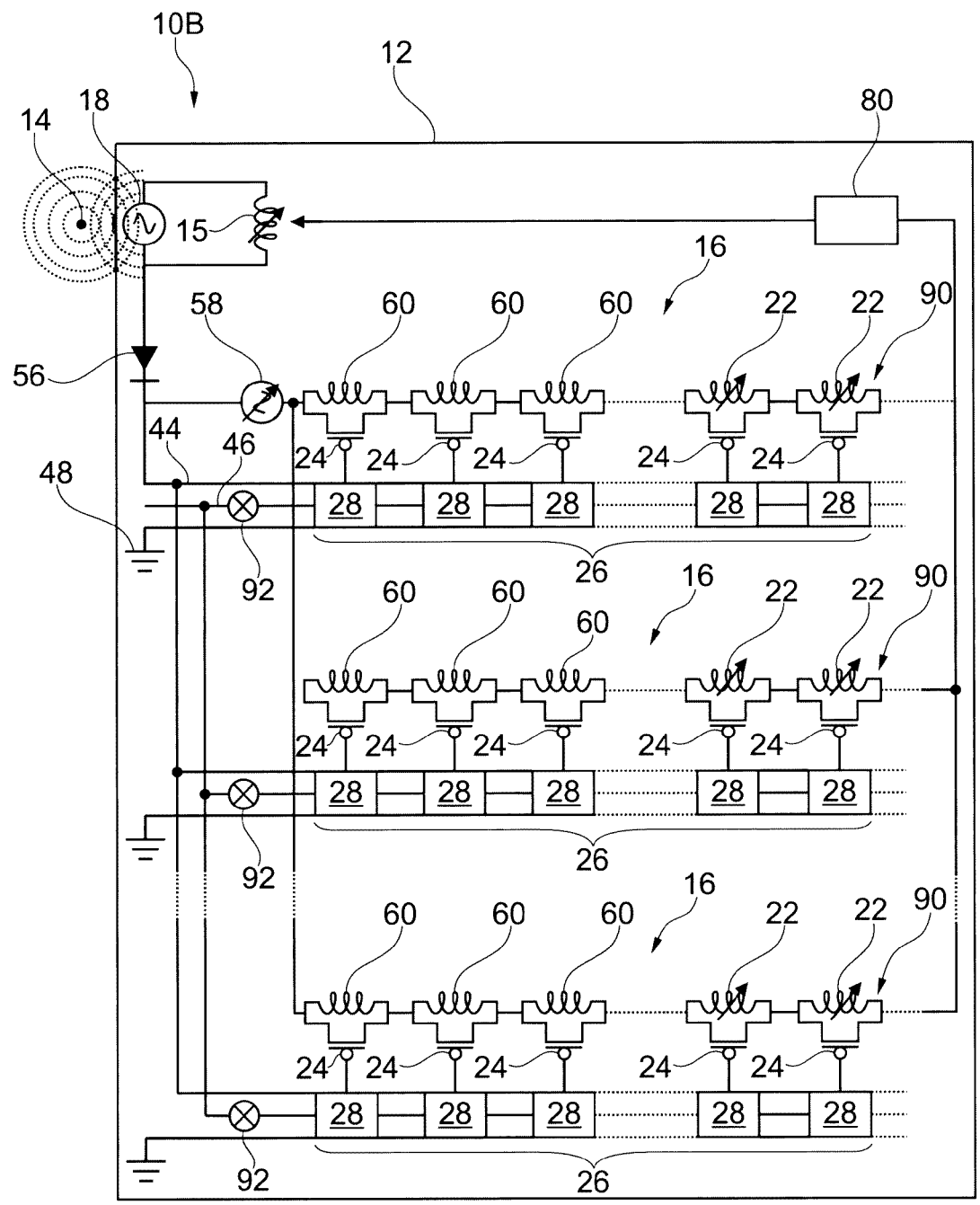
FIGS. 11 and 12 illustrate two examples of electrical circuits having a plurality of measurement lines.

In FIG. 11, an electrical diagram of an alternative electrical circuit 10B of the electrical circuit 10 in FIG. 1 has been represented. This electrical diagram 10B is distinguished from the electrical circuit 10 in FIG. 1 in that it includes a plurality of measurement lines 90, mounted in parallel, where the electrical circuit 10 in FIG. 1 merely includes a single line. Herein, the measurement lines 90 are identical to the single line represented in FIG. 1. The measurement circuit 16 includes however line selectors 92, to carry out the measurement in each of the lines independently from the other lines 90, particularly each line in succession from one another. The line selectors 92 may adopt a substantially identical form to the control modules 28, thereby supplying each line 90 with current, successively.

In the example shown, an analogue/digital converter 80 is also provided between the parallel branches formed by the measurement lines 90 and the variable impedance 15.

Figure 12:
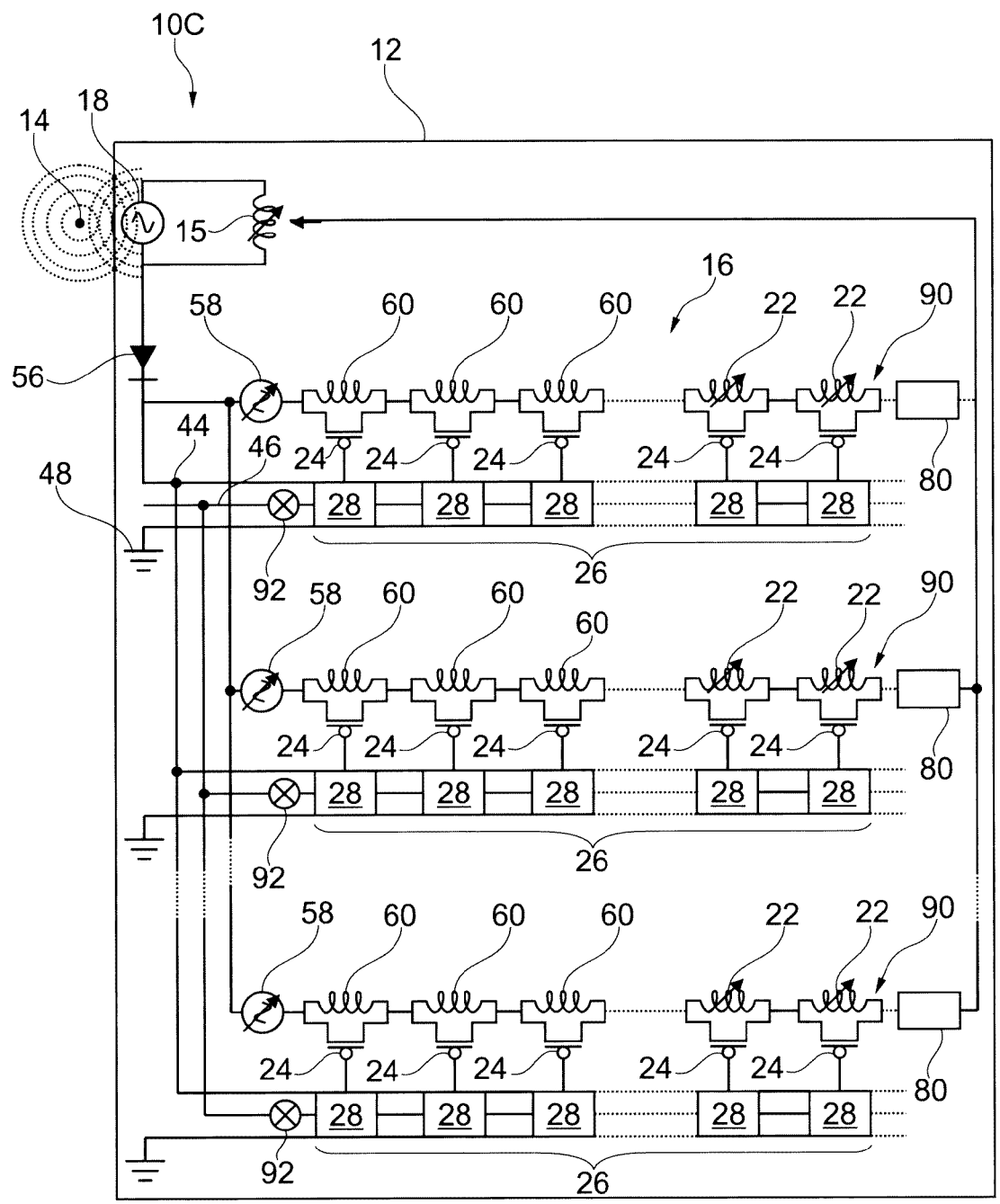

The electrical circuit 10C illustrated in FIG. 12 is similar to the electrical circuit 10B in FIG. 11. It is essentially distinguished by the presence of an analogue/digital converter 80 on each of the measurement lines 90 in parallel.

It should be noted that it is also possible to envisage electrical circuits with a plurality of measurement lines 90 on the basis of the electrical circuits 100 and 200 in FIGS. 3 and 4.

It is also possible to envisage elements 60A of known and fixed impedance between each of the sensors on each of these lines or on certain lines only. It is then possible to identify the line wherein the measurement is made at each time by choosing unique combinations of impedances 60 at the start of the line 90 for each line 90.

In the scenario where the electrical circuit 10B, 10C includes a plurality of measurement lines, it has been determined that it is particularly advantageous that the measurement lines extend on the medical device 12, particularly on the stent 12 in imbricated coaxial helices. In other words, the measurement lines extends in parallel along helices wound around one another. Indeed, this makes it possible to minimise the distance between sensors of different lines. This is particularly advantageous because if a sensor 22 of a line 90, or even the entire line 90 is defective, the missing value(s) may be better approximated by the values measured with the other measurement line(s), of which one or a plurality of sensors are situated in the vicinity. The device 12 thereby gains in robustness, which is particularly advantageous when it is implanted in a patient's body.

It should be noted that the electrical circuits described are suitable for determining for each sensor of the electrical circuits, the value measured thereby. The position of the sensors on the medical device, particularly on the stent, being known, it is possible to determine a model representing in real time, the progression of the physical parameters measured on the medical device. As such, a practitioner may obtain real-time information. This information may particularly relate to the correct positioning of the medical device, particularly of the stent, in a cavity of the human body. Representing the pressures measured by pressure sensors arranged on the outer surface of the medical device, particularly of the stent, can enable the practitioner to determine whether this medical device is correctly implanted or not: a measured pressure that is too low, for example, may indicate that the stent is not in contact with the wall of the cavity receiving same.

The processing unit of the medical system described above, comprising for example an electronic control unit and a screen, or a computer, may be suitable for determining a real-time model, for example a 3D model, based on the values measured and displaying the model on the screen. The values between the measurement points may, in this case, be approximated, particularly by convolution according to the distance to the closest measurement points.

Various visual and/or acoustic signals may be emitted by the processing unit, in the scenario where at least one measured value does not meet expectations. The visual signals may particularly be suitable for identifying on the model shown, the sensors 22 for which the measured values are not conforming.

Alternatively, the processing unit may process the digital values measured, compare them to expected value ranges and display as an output in a different manner, the points where the measurement is within the ranges and the points where the measurement is not within the ranges, for example by using different display colours.

The visual signals complete the display of the model described above.

The invention is not restricted solely to the examples of embodiments described above with regard to the figures, by way of illustrative and non-restrictive examples.

In particular, the implantable medical device may be chosen from the group comprising:
  a heart valve,
  a cardiac stimulator,
  a cochlear implant,
  a throat implant,
  an orthopaedic implant,
  a brain implant,
  a retinal implant,
  a catheter, or
  a cellular tissue ("tissue-engineered construct").

Alternatively, the medical device may not be implantable. It can then, in particular, be applied on a part of the human body. The medical device may in this case take the form of a dressing, bandage or strip to be applied onto a patient's skin. The medical device may also take the form of a contact lens to be placed on a patient's cornea.

Finally, according to a further alternative embodiment, the medical device may be neither implantable in the human body, not applicable thereon.

The invention claimed is:

1. A medical device comprising:
an electrical measurement circuit comprising a plurality of variable-impedance sensors to detect a physical quantity of a tissue and a plurality of switches, the plurality of variable-impedance sensors being arranged in a plurality of measurement lines, wherein each measurement line of the plurality of measurement lines comprises at least two variable-impedance sensors arranged in series, and wherein each sensor of the plurality of variable-impedance sensors is associated with a switch, of the plurality of switches, to regulate a power supply to the sensor;
an electrical power source to supply power to the electrical measurement circuit;
an antenna to emit an electromagnetic field according to an impedance of the electrical measurement circuit, the impedance of the electrical measurement circuit varying over time according to which of the plurality of variable-impedance sensors is powered at a time, and
at least one control circuit to control opening and/or closing of the plurality of switches according to one or more configurations, to operate the plurality of variable-impedance sensors of the electrical measurement circuit.

2. The medical device according to claim 1, wherein the at least one control circuit comprises a plurality of control circuits, at least some of the plurality of control circuits arranged in series with respect to one another, each control circuit of the plurality of control circuits controlling an associated switch of the plurality of switches.

3. The medical device according to claim 2, wherein:
each control circuit, of the plurality of control circuits, comprises a series RC circuit, and
the plurality of control circuits and the plurality of switches are arranged such that charging and/or discharging of a control circuit, of the plurality of control circuits, triggers closing and/or opening of a switch, of the plurality of switches, associated with the control circuit.

4. The medical device according to claim 3, wherein the plurality of control circuits are arranged in a series arrangement such that charging or discharging of a first series RC circuit of a first control circuit, of the plurality of control circuits, induces charging or discharging of a second series RC circuit of a second control circuit, of the plurality of control circuits, wherein the first control circuit precedes the second control circuit in the series arrangement of the plurality of control circuits.

5. The medical device according to claim 4, wherein the first control circuit of the plurality of control circuits comprises:
a first transistor comprising a source connected to an input of the first control circuit, a gate connected to an output of the first control circuit, and a drain connected to a control terminal of the switch, of the plurality of switches, with which the first control circuit is associated,
a first inverter comprising an input connected to the input of the first control circuit and an output connected to a first terminal of a resistor of the series RC circuit of the first control circuit,
a second terminal of the resistor being connected to a first terminal of a capacitor of the series RC circuit of the first control circuit and a second terminal of the capacitor being connected to ground,
a second inverter comprising an input connected to the second terminal of the resistor and an output connected to the output of the first control circuit, and
said output of the first control circuit being connected to an input of the second control circuit of the plurality of control circuits.

6. The medical device according to claim 4, wherein the first control circuit of the plurality of control circuits comprises:
a first transistor comprising a gate connected to an input of the first control circuit and a drain connected to a positive power supply terminal,
a second transistor comprising a source connected to a source of the first transistor, a gate connected to an output of the first control circuit, and a drain connected to a first terminal of a variable-impedance sensor with which the first control circuit is associated,
a second terminal of the variable-impedance sensor being connected to the ground,
a diode comprising an anode connected to the source of the first transistor and a cathode connected to a first terminal of a resistor of a series RC circuit of the first control circuit,
a second terminal being connected to the output of the first control circuit,
a capacitor of the series RC circuit being connected between the output of the first control circuit and the ground.

7. The medical device according to claim 1, wherein:
the medical device comprises a plurality of sets, each set of the plurality of sets comprising a switch of the plurality of switches and a sensor of the plurality of variable-impedance sensors,
a first plurality of sets, of the plurality of sets, are arranged in a first measurement line of the plurality of measurement lines,
the plurality of measurement lines are arranged in parallel to one another,
the first plurality of sets are arranged in series in the first measurement line, and
in each set of the first plurality of sets, a switch and a sensor are arranged in parallel with respect to one another.

8. The medical device according to claim 1, wherein:
the medical device comprises a plurality of sets, each set of the plurality of sets comprising a switch of the plurality of switches and a sensor of the plurality of variable-impedance sensors,
a first plurality of sets, of the plurality of sets, are arranged in a first measurement line of the plurality of measurement lines,
the plurality of measurement lines are arranged in parallel to one another,
the first plurality of sets are arranged in parallel in the first measurement line, and
in each set of the first plurality of sets, a switch and a sensor are arranged in series with respect to one another.

9. The medical device according to claim 1, wherein at least one sensor of the plurality of variable-impedance sensors is arranged on an outer surface of the medical device to contact at least a part of a tissue contacted by the at least one of the plurality of sensors.

10. The medical device of claim 1, wherein the at least one control circuit is arranged to control the opening and/or the closing of the plurality of switches over time to adjust an impedance over the time of the electrical measurement circuit and to adjust the electromagnetic field emitted by the antenna over the time.

11. The medical device according to claim 1, wherein:
the medical device comprises a first end and a second end; and
the medical device further comprises a first pressure sensor and a second pressure sensor, the first pressure sensor arranged at the first end of the medical device and the second pressure sensor arranged at the second end of the pressure sensor.

12. The medical device according to claim 1, wherein:
the medical device comprises a mesh body, and
at least one sensor of the plurality of sensors is arranged at a mid-point of a structural member of the mesh body between contact points of the structural member of the mesh body with one or more other structural members of the mesh body.

13. The medical device according to claim 1, wherein the plurality of measurement lines extend along coaxial helices.

14. A medical system comprising:
the medical device according to claim 1; and
an interrogator to receive information encoded in the electromagnetic field emitted by the antenna of the medical device.

15. The system according to claim 14, wherein the interrogator further comprises:
a second antenna to emit an electromagnetic field to create an induced current in at least one component of the electrical power source of the medical device.

16. The system according to claim 15, wherein the medical further comprises:
one or more fixed impedances; and
a comparator to compare an identifier emitted by the interrogator with a binary code associated with at least one of the one or more fixed impedances and to operate the electrical measurement circuit based at least in part on an output of the comparator.

17. The system according to claim 14, further comprising:
at least one computing device to process information received by the interrogator, the at least one computing device comprising a screen to display, based on processing of the information received from the medical device, a model of the medical device comprising information relating to values of measurements made using at least some of the plurality of variable-impedance sensors.

18. The medical device according to claim 10, wherein:
the electrical measurement circuit includes a plurality of fixed impedances, each associated with a switch of the plurality of switches; and
the at least one control circuit is arranged to control the opening and/or closing the plurality of switches to cause the antenna to output, based at a time on one or more of the plurality of fixed impedances, one or more fixed values.

19. The medical device of claim 18, wherein the one or more fixed values comprise an identifier for the medical device.

20. The medical device of claim 18, wherein:
the at least one control circuit is arranged to control the opening and/or closing the plurality of switches to cause the antenna to output, based at a time on one or more of the plurality of variable-impedance sensors, one or more variable values; and
the one or more fixed values comprise a fixed value to be output by the antenna between two variable values.

21. A method of transmitting measurements from a medical device disposed within a body and in contact with one or more tissues of the body, the medical device comprising a plurality of variable-impedance sensors and a plurality of switches, the plurality of variable-impedance sensors being arranged in the medical device in a plurality of measurement lines, each measurement line of the plurality of measurement lines comprising at least two variable-impedance sensors of the plurality of variable impedance sensors arranged in series and each sensor of the plurality of variable-impedance sensors being associated with a switch, of the plurality of switches, to regulate a power supply to the sensor, wherein the plurality of variable-impedance sensors and the plurality of switches are selectively electrically connected between a power source of the medical device and an antenna of the medical device, the method comprising:
emitting from the medical device, via an antenna of the medical device, measurements of impedance of the one or more tissues contacted by the medical device, wherein emitting the measurements of impedance from the medical device comprises:
successively coupling variable-impedance sensors, of the plurality of variable-impedance sensors, between the power source and the antenna such that at a time an electrically conductive path is formed between the power source and the antenna via a variable-impedance sensor coupled between the power source and the antenna at the time and such that an impedance of the variable-impedance sensor regulates an electrical signal conveyed on the electrically conductive path, and
at a time that a variable-impedance sensor of the plurality of variable-impedance sensors is coupled between the power source and the antenna, applying at least one electrical signal at a frequency to the body;
wherein successively coupling the variable-impedance sensors comprises successively coupling the variable-impedance sensors in accordance with the plurality of measurement lines into which the plurality of variable-impedance sensors are arranged to successively couple all one or more variable-impedance sensors of one measurement line before successively coupling any of one or more variable-impedance sensors of another measurement line.

22. The method of claim 21, wherein:
the medical device comprises a plurality of fixed impedances selectively electrically connected between a power source of the medical device and an antenna of the medical device, each fixed impedance of the plurality of fixed impedances being associated with a switch, of the plurality of switches, to regulate a power flow via the fixed impedance; and
the method further comprises emitting from the medical device, via the antenna, an electrical signal based on an arrangement of fixed impedances selectively coupled between the power source and the antenna at a time, wherein emitting the electrical signal comprises selectively coupling at the time one or more of the plurality of fixed impedances between the power source and the antenna at the time.

23. The method of claim 22, wherein emitting the electrical signal comprises emitting the electrical signal interleaved between emissions of measurements of impedance emitted from the medical device.

24. The method of claim 23, wherein:
the one or more of the plurality of fixed impedances is one fixed impedance;
the one fixed impedance is arranged in a first measurement line, of the plurality of measurement lines, in series between a first variable-impedance sensor and a second variable-impedance sensor of the measurement line;
emitting the electrical signal interleaved between emissions of measurements of impedance comprises emitting the electrical signal interleaved between emission of a first measurement of impedance from the first variable-impedance sensor and emission of a second measurement of impedance from the second variable-impedance sensor; and
emitting the electrical signal comprises emitting a calibration signal.

25. The method of claim 22, wherein emitting the electrical signal comprises emitting an identifier for the medical device.

26. The method of claim 21, wherein successively coupling variable-impedance sensors comprises coupling a variable-impedance sensor by opening a switch that is arranged to short-circuit the variable-impedance sensor when closed.

* * * * *